US00PP31189P2

(12) United States Plant Patent
Kordes

(10) Patent No.: US PP31,189 P2
(45) Date of Patent: Dec. 10, 2019

(54) MINIATURE ROSE PLANT NAMED 'KORONE006'

(50) Latin Name: *Rosa hybrida*
Varietal Denomination: KORone006

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/998,225

(22) Filed: Jul. 19, 2018

(30) Foreign Application Priority Data

May 28, 2018 (QZ) ..... PBR 2018/1393

(51) Int. Cl.
*A01H 5/02* (2018.01)
*A01H 6/74* (2018.01)

(52) U.S. Cl.
USPC ..... Plt./118

(58) Field of Classification Search
USPC ..... Plt./101, 116, 118
See application file for complete search history.

(56) References Cited

U.S. PATENT DOCUMENTS

PP19,638 P2 1/2009 Kordes

*Primary Examiner* — Susan McCormick Ewoldt
(74) *Attorney, Agent, or Firm* — Buchanan Ingersoll & Rooney PC

(57) ABSTRACT

A new and distinct variety of Miniature Rose Plant, herein referred to by its cultivar name, 'KORone006', is provided which forms attractive, double, yellow colored blossoms. The vegetation is vigorous and the growth habit is upright. Attractive ornamental foliage is formed. The new variety is particularly well suited for providing distinctive ornamentation in the landscape.

1 Drawing Sheet

Botanical/commercial classification: Latin name—*Rosa hybrida*. Common name—Miniature Rose Plant. Varietal Denomination—'KORone006'.

CROSS-REFERENCE TO RELATED APPLICATIONS

This application claims priority to Plant Breeders' Right Application Number 2018/1393, which was filed at Community Plant Variety Office in the European Union on May 28, 2018, the contents of which are hereby incorporated by reference for all purposes.

SUMMARY OF THE INVENTION

The new variety of *Rosa hybrida* Miniature Rose Plant of the present invention was created during 2013 at Offenseth-Sparrieshoop, Germany by artificial pollination wherein two parents were crossed which previously had been studied in the hope that they would contribute the desired characteristics. The female parent (i.e., seed parent) of the new variety was an unnamed seedling (non-patented in the United States). The male parent (i.e., pollen parent) of the new variety was the 'KORpedia' variety (U.S. Plant Pat. No. 19,638).

The parentage can be summarized as follows:

unnamed seedling×'KORpedia'

The seeds resulting from the above pollination were sown and small plants were obtained which were physically and biologically different from each other. Selective study resulted in the identification of a single plant of the new variety.

It was found that the new Miniature Rose Plant of the present invention possesses the following combination of characteristics:

(a) forms attractive, double, yellow colored blossoms,
(b) exhibits an upright growth habit,
(c) forms vigorous vegetation, and
(d) forms attractive ornamental foliage.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the unnamed seedling seed parent exhibits a darker yellow colored flower and smaller flowers compared to the new variety; also the unnamed seedling seed parent exhibits a medium, bushy growth habit, while the new variety exhibits an upright growth habit. Additionally, the 'KORpedia' variety (i.e., pollen parent) exhibits white colored flowers, an upright to bushy growth habit and is moderately fragrant, while the new variety exhibits yellow colored flowers, an upright growth habit, and lacks a fragrance. Moreover, the new variety can be readily distinguished from non-parental related similar varieties. For example, the 'Wekamanda' variety (U.S. Plant Pat. No. 9,591) exhibits larger diameter flowers with higher number of petals compared to the new variety, and displays a less brilliant yellow colored petal when opening compared to the new variety.

The new variety has been found to undergo asexual propagation in Klein Offenseth-Sparrieshoop, Germany by a number of routes such as vegetative cuttings. Asexual propagation techniques in Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORone006'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Klein Offenseth-Sparrieshoop, Germany while growing indoors on its own roots in 6.0 cm containers.

FIG. 1—illustrates a specimen of a blossom.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms.

The description is based on the observation of a one-year-old specimen of the new variety, observed during February, while growing in a one-gallon container on its own roots in a greenhouse at Cochranville, Pa.

Class: Miniature Rose Plant.

Plant:

*Habit.*—Very upright.

*Height.*—Approximately 50.0 cm on average.

*Width.*—Approximately 30.0 cm on average.

Branches:

*Immature stem color.*—Commonly near Yellow-Green Group 144A.

*Mature stem color.*—Commonly near Brown Group 200D.

*Main stem length.*—Approximately 50.0 cm on average.

*Secondary stem length.*—Approximately 20.0 cm on average.

*Surface texture.*—Immature stems: glabrous mature stems: smooth to rough where the wood is becoming harder.

*Thorns.*—Young thorns: moderate amount; length is approximately 3.0 mm on average, width is approximately 1.0 mm at point of attachment on average, and color is commonly near Greyed-Orange Group 166A. old thorns: moderate amount; length is approximately 6.0 mm on average, width is approximately 5.0 mm at point of attachment on average, and color is commonly near Greyed-Red Group 181.

Foliage:

*General appearance.*—Ornamental.

*Young foliage.*—Upper surface color. commonly near Yellow-Green Group 144A, with venation of near Green Group 141A and near Greyed-Orange Group 176A at the margin. under surface color. commonly near Green Group 142C with venation of near Green Group 1142B.

*Old foliage.*—Upper surface color. commonly near Yellow-Green Group 146B with venation of near Green Group 137A. under surface color. commonly near Green Group 138B.

*Petioles.*—Upper surface: texture is smooth, color is commonly near Green Group 137A. under surface: texture is mostly smooth with sparse prickles, color is commonly near Yellow-Green Group 144A.

*Rachis.*—Color upper surface is commonly between near Brown Group 200C and Green Group 137A, under surface is commonly near Yellow-Green Group 144A.

*Stipules.*—Length: approximately 1.0 cm on average. width: approximately 2.0 mm on average. margin: entire to erose. color upper surface is commonly near Yellow-Green Group 144A; under surface is commonly near Yellow-Green Group 144B.

*Leaf margin.*—Serrate.

Leaflets:

*Number.*—3, 5, and 7.

*Arangement.*—Odd pinnate.

*Shape.*—Ovate; apex is acute; and base is rounded.

*Venation.*—Pattern is reticulate.

*Texture.*—Upper surface is smooth; lower surface is smooth.

*Glossiness.*—Upper side of leaf is semi-glossy.

*Size.*—Terminal leaflet: length is approximately 4.0 cm on average and width is approximately 3.0 cm on average. lower leaflets: length is approximately 2.2 cm on average and width is approximately 1.2 cm on average. 5-Leaflet leaf: length is approximately 10.5 cm on average and width is approximately 6.0 cm on average.

Inflorescence:

*Number of flowers.*—Approximately 1 to 3 open blooms on average on a plant at once.

*Number of blooms per stem.*—Commonly 1 bloom per stem on average.

*Peduncle.*—Color commonly Yellow-Green Group N144A. diameter approximately 1.0 cm on average. length: approximately 6.0 cm on average. surface texture: glabrous. strength: strong.

*Sepals.*—Number commonly 5. upper surface color and texture: covered in short pubescence and color is commonly near Yellow-Green Group 144A. under surface color and texture: puberulent and color is commonly near Yellow-Green Group 144A. size: length is approximately 3.0 cm on average and width is approximately 1.0 cm on average. shape: lanceolate; apex is acute to aristate; base is truncate or flat as it joins the receptacle. margin: entire with occasional extensions on two or three sepals measuring approximately 7.0 mm in length and approximately 1.0 mm in width.

*Bud.*—Shape: globular. size: length is approximately 1.5 cm on average; width is approximately 1.5 cm on average.

*Flower.*—double, yellow colored. no fragrance. form: double, cuplike profile: flat. diameter approximately 9.0 cm on average. height: approximately 3.5 cm on average. duration: commonly on the plant approximately 35 days on average. petal color when first and fully open: upper surface is commonly near Yellow Group 3A with a small basal spot of near Yellow Group 7B; under surface is commonly near Yellow Group 3B. petal color when fading: upper surface is commonly near Yellow Group 4D with a small basal spot of near Yellow Group 4B and under surface is commonly near White Group 155A.

*Petal.*—Number approximately 38 on average. drop: good. length: inner petals are approximately 4.0 cm on average and outer petals are approximately 4.0 cm on average. width: inner petals are approximately 2.7 cm on average and outer petals are approximately 4.5 cm on average. shape: overall shape is broadly obovate; apex is round; and base is cuneate. texture: upper and under surface is glabrous. margin: entire.

*Petaloids.*—Number approximately 10 per flower on average. color. upper and under surfaces are commonly near Yellow Group 12A. size: length is approximately 2.0 cm on average and width is approximately 6.0 mm on average. texture: smooth. margins: variable, entire to erose. shape: variable, oblong and mostly curving inward; apex is round, and base is cuneate.

*Stamen.*—Number approximately 80 on average. anthers: number is about 80 and color is commonly near Yellow Group 4D toward the central portion and near Yellow Group 13A along the margins; length is approximately 2.0 mm on average; and shape is oval. filaments: length is approximately 4.0 mm to 5.0 mm on average and color is commonly near Yellow Group 7A.

*Pistils.*—Arrangement: separate and free. number approximately over 100 on average. style: color is mostly near Greyed-Yellow Group 162D and length is approximately 5.0 mm on average. stigma: color is commonly near Green-Yellow Group 1A, diameter is typically less than 1.0 mm, and shape is fan shaped.

*Ovary.*—Length is approximately 3.0 mm, width is approximately 1.0 mm, and color is commonly near White Group 155D.

*Receptacle.*—Achenes stand on the bottom and wall; diameter is approximately 8.0 mm on average, shape is urn shaped, color is commonly near Yellow-Green Group 144A, and surface texture is smooth.

*Pollen.*—None observed.

*Hips/seed.*—None observed.

Development:

*Vegetation.*—Dark green, vigorous, and strong.

*Blooming.*—Produces few large individual blooms at a given time and will rebloom again in the same season.

*Winter hardiness.*—Unknown.

*Resistance to disease.*—Good resistance to Botrytis (Botrytis cinerea) disease under normal greenhouse growing conditions in Cochranville, Pa.

Plants of the 'KORone006' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) forms attractive, double, yellow colored blossoms, (b) exhibits an upright growth habit, (c) forms vigorous vegetation, and (d) forms attractive ornamental foliage;

substantially as herein shown and described.

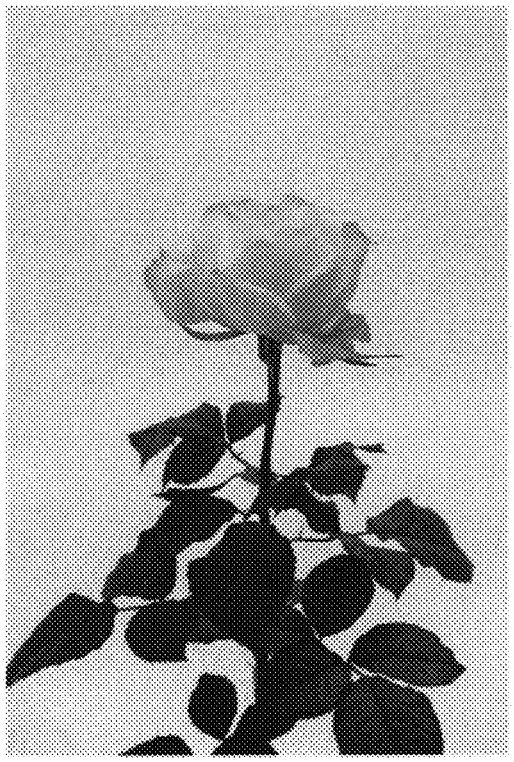

* * * * *